United States Patent [19]

Ashida et al.

[11] Patent Number: 5,585,248
[45] Date of Patent: Dec. 17, 1996

[54] METHOD FOR ASSAYING ACTIVITY OF PROPHENOLOXIDASE ACTIVATING ENZYME AND APPLICATION THEREOF

[75] Inventors: Masaaki Ashida, Sapporo; Tomohisa Kawabata, Amagasaki; Kazunari Hirayasu, Amagasaki; Masakazu Tsuchiya, Amagasaki, all of Japan

[73] Assignee: Wako Pure Chemical Industries, Ltd., Osaka, Japan

[21] Appl. No.: 343,943

[22] Filed: Nov. 17, 1994

[30] Foreign Application Priority Data

Nov. 18, 1993 [JP] Japan .................. 5-289513

[51] Int. Cl.[6] .............. C12Q 1/26; C12Q 1/00; C12Q 1/48; C12Q 1/34
[52] U.S. Cl. .............. 435/25; 435/4; 435/15; 435/16; 435/18; 435/201; 435/206; 436/63; 530/300; 530/812
[58] Field of Search ............... 435/25, 4, 19, 435/23, 16, 18, 201, 206; 436/63; 530/300, 812

[56] References Cited

U.S. PATENT DOCUMENTS 4,970,152  11/1990  Ashida et al. .............. 435/25

OTHER PUBLICATIONS

Ashida, M., Insect Biochem, vol. 11, pp. 57–65, 1981.
Ashida, M. et al, "Biochem. Biophys. Res. Comm.", vol. 113, No. 2, pp. 562–568 (1983).
Yoshia et al, "Biochem. Biophys. Res. Comm.", 1986, pp. 1177–1184.

*Primary Examiner*—John Kight
*Assistant Examiner*—Louise Leary
*Attorney, Agent, or Firm*—Sughrue, Mion, Zinn, Macpeak & Seas

[57] ABSTRACT

A method for assaying an activity of a prophenoloxidase activating enzyme (PPAE), comprising assaying at least X-Arg or Y produced upon contact of the PPAE with a peptide chain of the formula X-Arg-Y wherein X is an optionally labeled amino acid residue or peptide residue, having an optionally protected α-amino group or N-terminal, provided that the amino acid residue adjoining Arg is not Gly or Ala, and Y is an organic residue capable of binding to a carboxyl group of Arg by acid amide bonding or ester bonding, or an optionally labeled amino acid residue or peptide residue, having an optionally protected α-carboxyl group or C-terminal, the peptide chain capable of being hydrolyzed into X-Arg and Y by a PPAE derived from an insect. According to the present invention, PPAE activity can be quantitatively assayed with precision and a highly precise method for determining β-1,3-glucan and/or peptidoglycan, wherein said PPAE activity is used as an index, can be provided. In addition, the present invention enables detection of fungi and bacteria without multiplication by culture, which makes early diagnosis of microbial infections possible. The present invention is applicable to a wide range of use such as tests for microbial contamination of water and food, safety tests of therapeutic agents such as antibiotics and injectable preparations, etc.

10 Claims, 6 Drawing Sheets

F I G. 1
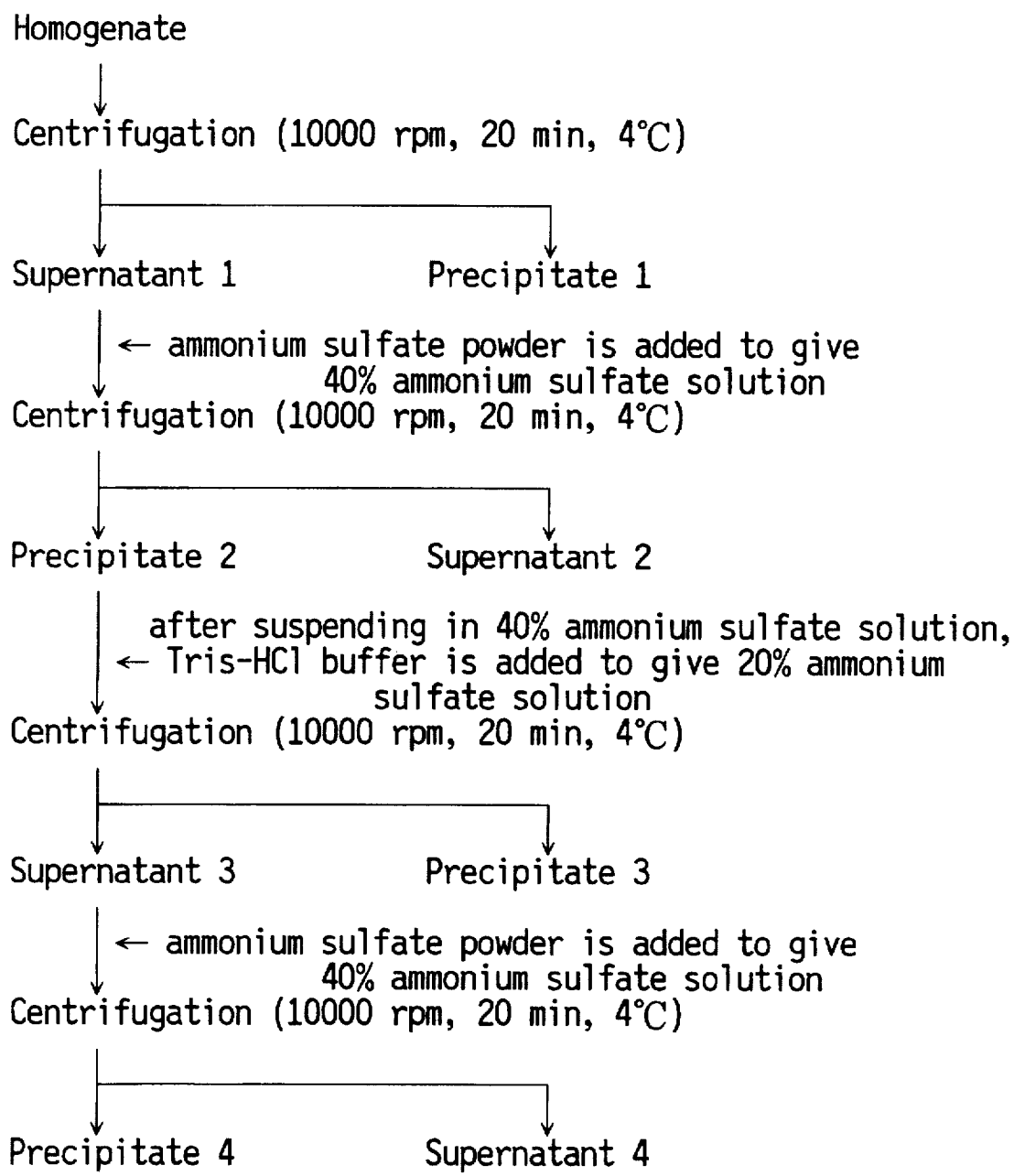

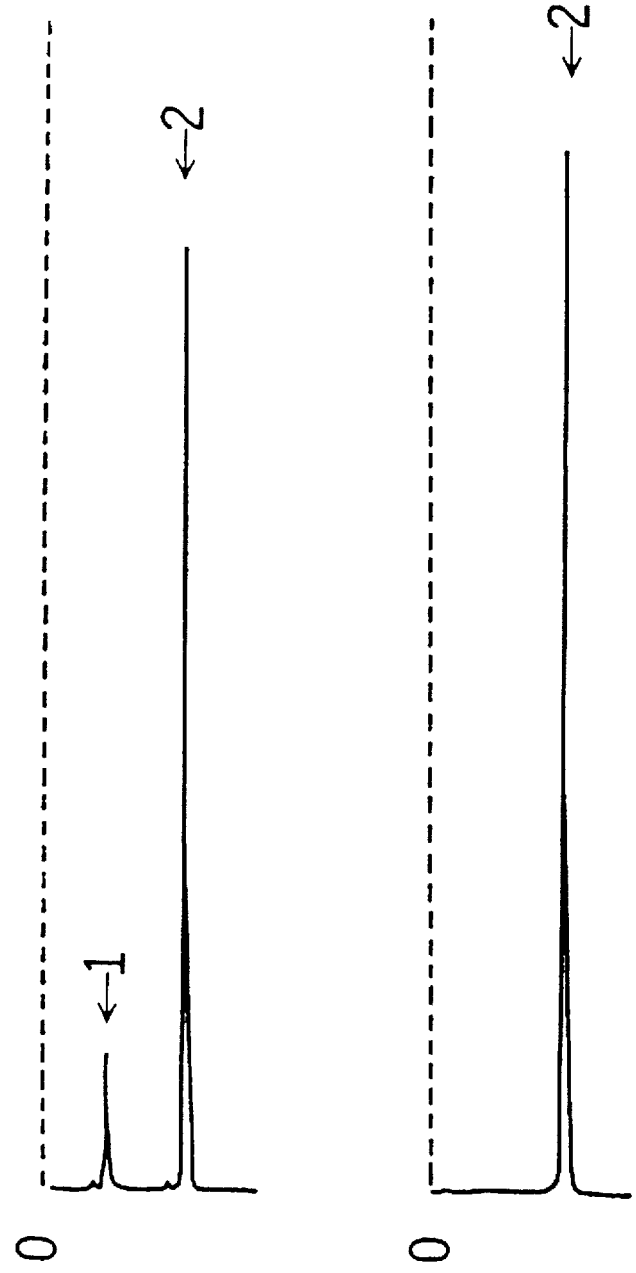

5,585,248

METHOD FOR ASSAYING ACTIVITY OF PROPHENOLOXIDASE ACTIVATING ENZYME AND APPLICATION THEREOF

FIELD OF THE INVENTION

The present invention relates to a method for assaying the activity of prophenoloxidase activating enzyme (hereinafter referred to as PPAE) and a method for assaying β-1,3-glucan and peptidoglycan by utilizing said assay method.

BACKGROUND OF THE INVENTION

A cascade involving a series of enzymes and called prophenoloxidase activating system (hereinafter referred to as proPO activating system), which is concerned with melanin formation in body fluid, exists in the body fluid of insects and β-1,3-glucan, a fungal cell wall component, and peptidoglycan, a bacterial cell wall component, are known to trigger said cascade [Onishi, Annot. Zool. Jpn., 27, 33–39 (1954), Ashida and Onishi, Arch. Biochem. Biophys., 122, 411–416 (1967), Brunet, Insect Biochem., 10, 467–500 (1980); Ashida and Yamazaki, Molting and Metamorphosis, 239–265, Japan Sci. Soc. Press (1990)]. This action is ascribed to β-1,3-glucan recognition protein (BGRP; molecular weight 62 kD) exhibiting specific affinity to β-1,3-glucan and peptidoglycan recognition protein (PGRP; molecular weight 19 kD) exhibiting specific affinity to peptidoglycan, which are present in said proPO activating system. When β-1,3-glucan or peptidoglycan is recognized by either protein, a series of cascade reactions begins. Through some unelucidated reactions inclusive of the reaction of an enzyme requiring $Ca^{2+}$, a PPAE which converts prophenoloxidase (precursor of phenoloxidase, hereinafter referred to as proPO) to phenoloxidase (hereinafter referred to as PO) is produced [Ashida and Dohke, Insect Biochem., 10, 37–47 (1980)].

In view of such phenomenon, various studies have been done in an attempt to establish a method for detecting bacterial infections and fungal infections, and safety tests of therapeutic agents by assaying β-1,3-glucan and peptidoglycan based on said cascade reaction.

Currently, Limulus test reagents, using amebocyte lysate from horseshoe crab (*Limulus polyphemus*, *Tachypleus tridentatus*) also having an in vivo cascade similar to that of insects, have been used as reagents for detecting bacterial infections and safety tests of therapeutic agents etc. In the absence of a system which reacts with peptidoglycan in horseshoe crab, however, detection is possible only for β-1,3-glucan and lipopolysaccharides, excluding Gram positive bacteria having no lipopolysaccharides. In addition, the reagent supplier horseshoe crab (*Tachypleus tridentatus*) is limited in number in Japan and unstable future supply thereof will always pose a difficulty.

When the cascade (proPO activating system) of insects is utilized, on the other hand, stable supply of reagents, as well as detection of bacteria, not to mention fungi, inclusive of Gram positive and negative ones can be expected, since the cascade includes a system which responds to peptidoglycan. It is also possible to specifically assay β-1,3-glucan (fungus) and peptidoglycan (bacterium) independently by separating a component which specifically reacts with peptidoglycan or a component which specifically reacts with β-1,3-glucan from the body fluid (U.S. Pat. No. 4,970,152).

The assay method based on the cascade of insects includes a conventional method wherein β-1,3-glucan and peptidoglycan are detected by measuring PO activity developed upon conversion of proPO to PO by PPAE. This method is encountered with the problems of self-oxidation of PO (which is an unstable enzyme) and unattainable markedly enhanced detection sensitivity.

So as to solve such problems, Kenneth T. Soderhall proposes a method for measuring β-1,3-glucan and endotoxin (lipopolysaccharides) by assaying certain serine protease activity which activates PO, with the use of a synthetic peptide as a substrate (EP-A-96689). The substrate used in this method is constructed without considering the reaction specificity of PPAE, which catalyzes the conversion of proPO to PO, but based on the sole fact that PPAE is among serine proteases, and whether PPAE activity, let alone β-1, 3-glucan and endotoxin (lipopolysaccharides), can be determined with precision is moot.

SUMMARY OF THE INVENTION

Accordingly, an object of the present invention is to provide a method for assaying PPAE activity with precision, which is achieved based on the substrate specificity that PPAE inherently possesses and high reaction specificity.

Another object of the present invention is to provide a method for assaying β-1,3-glucan and peptidoglycan by utilizing said assay method for PPAE activity.

The present inventors have analyzed the primary structure of proPO, an inherent substrate for PPAE, and succeeded in elucidating the amino acid sequence of the region that PPAE recognizes and cleaves.

Based on such findings, the present invention relates to a method for assaying PPAE activity, comprising the use of a peptide chain inclusive of PPAE recognition-cleavage site on proPO, as a substrate, and a method for assaying β-1,3-glucan and/or peptidoglycan, comprising the use of the PPAE activity assayed by said method, as an index.

BRIEF DESCRIPTION OF THE DRAWINGS

FIG. 1 is a scheme showing the steps of ammonium sulfate fractionation for the purification of PPAE.

FIGS. 6A and 6B is a liquid chromatogram showing the detection of peptidoglycan by the use of a synthetic peptide as a substrate, wherein 1 is the peak of the reaction product (2-Pyr-Ala-Leu-Asn-Arg-OH) (see SEQ ID NO:1) and 2 is the peak of synthetic peptide (2-Pyr-Ala-Leu-Asn-Arg-Phe-Gly-OH) (see SEQ ID NO:2).

DETAILED DESCRIPTION OF THE INVENTION

Figure 2:
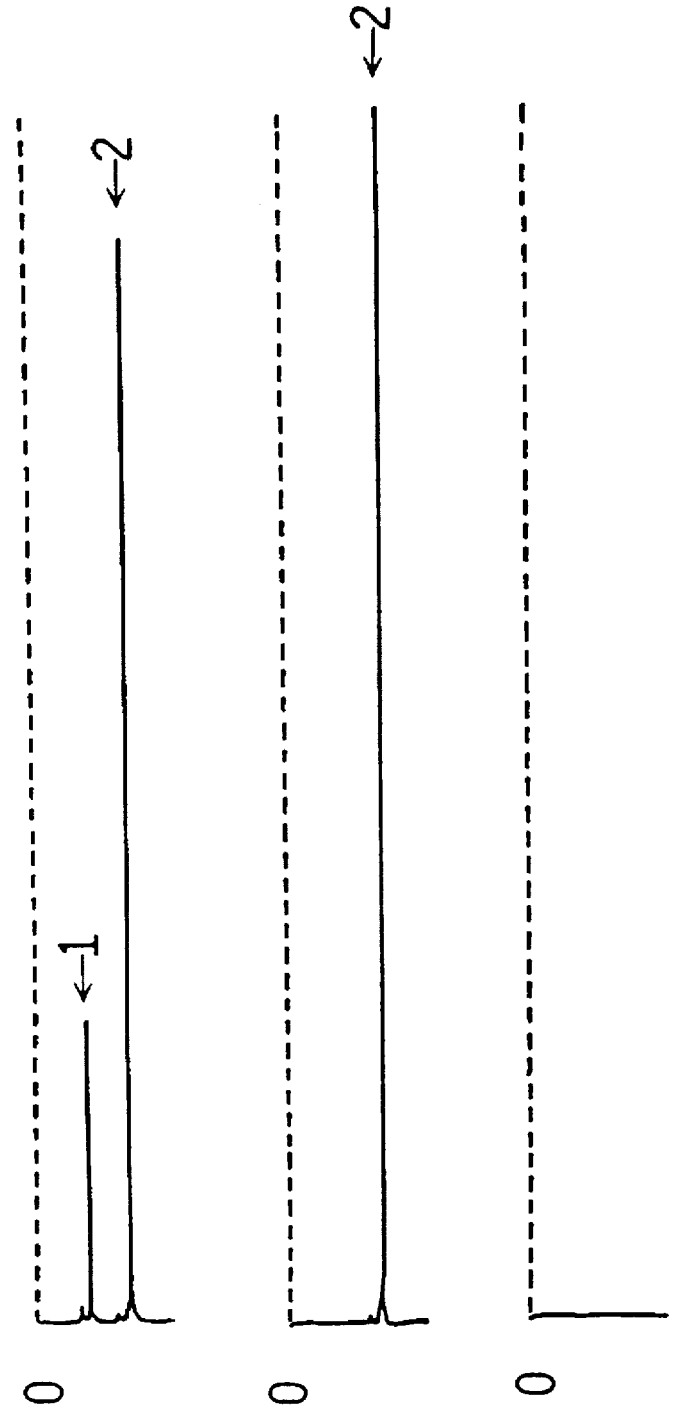
FIGS. 2A–2C shows analysis results of PPAE activity when a synthetic peptide was used as a substrate, as assayed by liquid chromatography, wherein 1 is a peak of the reaction product (2-Pyr-Ala-Leu-Asn-Arg-OH) (see SEQ ID NO:1) and 2 is a peak of the synthetic peptide (2-Pyr-Ala-Leu-Asn-Arg-Phe-Gly-OH) (see SEQ ID NO:1).

The present invention is a method for assaying PPAE activity, comprising assaying at least the below-mentioned X-Arg or Y produced upon contact of PPAE with a peptide chain of the formula (I)

X-Arg-Y     (I)

(see SEQ ID NO:3) wherein X is an optionally labeled amino acid residue or peptide residue, having an optionally protected α-amino group or N-terminal, provided that the amino acid residue adjoining Arg is not Gly or Ala, and Y is an organic residue capable of binding to a carboxyl group of Arg by acid amide bonding or ester bonding, or an optionally labeled amino acid residue or peptide residue, having an optionally protected α-carboxyl group or C-terminal, the peptide chain capable of being hydrolyzed into X-Arg and Y by a PPAE derived from an insect [hereinafter also referred to as Assay (1)]; particularly the method wherein said X is a group of the formula X'-Asn wherein X' is an optionally labeled amino acid residue or peptide residue, having an optionally protected α-amino group or N-terminal, with the proviso that X' has amino acids of the same number as X has less 1, or a protecting group for an amino group of Asn, and/or Y is a group of the formula Phe-Gly-Z (see SEQ ID NO:4) wherein Z is an optionally labeled amino acid residue or peptide residue, having an optionally protected α-carboxyl group or C-terminal, with the proviso that Z has amino acids of the same number as Y has less 2, or a protecting group for a carboxyl group of Gly. Moreover, the present invention relates to a method for assaying PPAE activity, comprising the use of a measurement method including ultraviolet or visible light absorbance, luminescence, fluorescence, radioactivity or magneticity.

The present invention is also a method for assaying β-1,3-glucan and/or peptidoglycan, comprising the use, as an index, of the PPAE activity determined by assaying at least X-Arg or Y produced upon contact of a proPO activating system and β-1,3-glucan and/or peptidoglycan, with a peptide chain of the formula (I)

X-Arg-Y     (I)

(see SEQ ID NO:3) wherein X is an optionally labeled amino acid residue or peptide residue, having an optionally protected α-amino group or N-terminal, provided that the amino acid residue adjoining Arg is not Gly or Ala, and Y is an organic residue capable of binding to a carboxyl group of Arg by acid amide bonding or ester bonding, or an optionally labeled amino acid residue or peptide residue, having an optionally protected α-carboxyl group or C-terminal, the peptide chain capable of being hydrolyzed into X-Arg and Y by a PPAE derived from an insect [hereinafter also referred to as Assay (2)]; particularly the method wherein said X is a group of the formula X'-Asn wherein X' is an optionally labeled amino acid residue or peptide residue, having an optionally protected α-amino group or N-terminal, with the proviso that X' has amino acids of the same number as X has less 1, or a protecting group for an α-amino group of Asn, and/or Y is a group of the formula Phe-Gly-Z (see SEQ ID NO:4) wherein Z is an optionally labeled amino acid residue or peptide residue, having an optionally protected α-carboxyl group or C-terminal, with the proviso that Z has amino acids of the same number as Y has less 2, or a protecting group for a carboxyl group of Gly. In addition, the present invention relates to a method for assaying β-1,3-glucan and/or peptidoglycan, comprising the use of a measurement method including ultraviolet or visible light absorbance, luminescence, fluorescence, radioactivity or magneticity.

Moreover, the present invention relates to a method for assaying β-1,3-glucan, comprising the steps of Assay (2), except that a proPO activating system obtained by removing a component which specifically reacts with peptidoglycan is used [hereinafter also referred to as Assay (3)] and a method for assaying peptidoglycan, comprising the steps of Assay (2), except that a proPO activating system obtained by removing a component which specifically reacts with β-1,3-glucan is used [hereinafter also referred to as Assay (4)].

The method for assaying PPAE activity of the present invention [Assay (1)] comprises measuring at least one of X-Arg and Y, which are reaction products obtained upon contact of PPAE with a substrate peptide chain: X-Arg-Y (see SEQ ID NO:3).

The substrate X-Arg-Y (see SEQ ID NO:3) is a peptide chain composed of two or more amino acid residues and is subject to no particular limitation insofar as it satisfies the following requirements.

A. Being decomposable into X-Arg and Y by a PPAE derived from an insect.

B. At least one of X-Arg and Y being measurable according to the chemical or physical properties thereof.

C. α-Amino group of Arg being bound with amino acid residue other than Gly and Ala.

As used herein, the peptide chain encompasses peptide and peptide derivatives. By peptide derivatives are meant those having protecting group at the N-terminal and/or the C-terminal of peptide, those having labeled amino acid residue, and the like.

X and Y binding to Arg are subject to no limitation insofar as they satisfy the above-mentioned requirements A. to C.

Examples of X include amino acid residues other than Gly and Ala, and peptide residues wherein the amino acid residue on the C-terminal side is not Gly or Ala. These amino acid residues and peptide residues may be labeled and α-amino group or N-terminal thereof may be protected.

X is preferably a group of the formula X'-Asn wherein X' is an optionally labeled amino acid residue or peptide residue, having an optionally protected α-amino group or N-terminal, provided that X' has amino acids of the same number as X has less 1, or a protecting group for α-amino group of Asn.

More preferably, X is a group having at least 2 amino acid residues on the C-terminal side of the amino acid sequence of proPO from silkworm (*Bombyx mori*), as depicted in the following.

X=Phe-Gln-Leu-Thr-Glu-Gln-Phe-Leu-Thr-Glu-Asp-Tyr-Ala-Asn-Asn-Gly-Ile-Glu-Leu-Asn-Asn (see SEQ ID NO:5)

or

X=Tyr-Gln-Arg-Val-Ser-Asn-Ala-Ile-Gly-Asn (see SEQ ID NO:6)

The number of amino acid residues is preferably 2 to 20.

As used herein, the protecting group for the N-terminal or α-amino group of peptide residue or amino acid residue and the protecting group for the α-amino group of Asn may be any group capable of protecting the α-amino group of amino acid residue, which is exemplified by carbobenzoxy, succinyl or alkoxycarbonyl having 2 to 18 carbon atoms.

Y of X-Arg-Y (see SEQ ID NO:3) is an organic residue capable of binding to the carboxyl group of Arg by acid amide bonding or ester bonding, or amino acid residue or peptide residue. These amino acid residue and peptide residue may be labeled and the α-amino group or C-terminal thereof may be protected.

By organic residue is meant that binding to the carboxyl group of Arg by acid amide bonding or ester bonding and which is released from X-Arg by the action of PPAE. The organic residue is subject to no particular limitation insofar as it can be detected physically or chemically, or insofar as its release from X-Arg-Y to give X-Arg and Y (see SEQ ID NO:3) (organic residue) causes different properties of the reaction system, which can be measured physically or chemically.

Examples thereof include, but not limited to, color developing groups such as p-nitroanilino group and 2-chloro-4-nitroanilino group, luminescent groups such as 2-pyridylamino, 3-pyridylamino, β-naphthylamino, 7-amino-4-methylcoumarin and 7-hydroxy-4-methylcoumarin, organic residues labeled with isotopes such as $^{125}I$, $^{14}C$ and $^{3}H$, and magnetic groups.

With regard to Y, peptide residue is preferably Phe-Gly-Z (see SEQ ID NO:4) wherein Z is an optionally labeled amino acid residue or peptide residue, having an optionally protected α-carboxyl group or C-terminal, provided that Z has amino acids of the same number as Y has less 2, or a protecting group for the carboxyl group of Gly.

More preferably, Y is a group having at least 2 amino acid residues on the N-terminal side of the amino acid sequence of proPO obtained from silkworm (*Bombyx mori*), as depicted in the following.

Y=Phe-Gly-Asp-Asp-Ala-Ser-Glu-Lys-Ile-Pro-Leu-Lys-Asn-Leu-Ser-Lys-Leu-Pro-Glu-Phe-Lys-Ile (see SEQ ID NO:7)

or

Y=Phe-Gly-Ser-Asp-Ala-Gly-Arg-Met-Ile-Pro (see SEQ ID NO:8)

The number of amino acid residues is preferably 2 to 20.

While the amino acid residue is not particularly limited, it is preferably Phe.

As used herein, the protecting group for the C-terminal or carboxyl group of peptide residue or amino acid residue, and the protecting group for the carboxyl group of Gly may be any group capable of protecting the α-carboxyl group of amino acid residue, which is typically exemplified by aralkyloxy such as benzyloxy or phenethyloxy.

In the present invention, the label is not particularly limited insofar as it modifies or substitutes a part of peptide residue or amino acid residue, as a result of which a compound having said peptide residue or amino acid residue can be determined.

The labeling substances include, for example, but not limited to, enzymes used in Enzyme Immunoassay, such as alkali phosphatase, β-galactosidase, peroxidase, micro peroxidase, glucoseoxidase, glucose-6-phosphoric acid dehydrogenase, malic acid dehydrogenase and luciferase; radioactive isotopes used in Radio Immunoassay, such as $^{99m}Tc$, $^{131}I$, $^{125}I$, $^{14}C$ and $^{3}H$; fluorescent substances such as 2-aminopyridine, 3-aminopyridine, and fluorescein, dansyl, fluorescamine, coumarin, naphthylamine and derivatives thereof used for Fluorescent Immunoassay; light emitting substances such as luciferine, isoluminol, luminol and bis(2,4, 6-trifluorophenyl)oxalate; substances showing absorption in the ultraviolet range, such as phenol, naphthol, anthracene and derivatives thereof; substances having spin labeling properties, such as compounds having oxyl group (e.g. 4-amino-2,2,6,6-tetramethylpiperidin-1-oxyl, 3-amino-2,2, 5,5-tetramethylpyrrolidin-1-oxyl, 2,6-di-t-butyl-α-(3,5-di-t-butyl-4-oxo-2,5-cyclohexadien-1-ylidene)-p-tolyloxyl).

While the insects (Insecta) from which PPAE derives are not subject to any particular limitation, those having well-established breeding methods are preferable. Examples thereof include lepidoptera such as silkworm moth (Bombycidae), tobacco horn worm (*Manduca sexta*), deptera such as housefly (*Musca domestics*), *Boettcherisca peregrina*, orthoptera such as *Locusts migratoria* and Emmafield cricket, and beetles (Coleoptera) such as *Acalolepta luxuriosa*.

Insects are used irrespective of their stages of development and they may be larvae or adults. The insects of lepidoptera, deptera and coleoptera are preferably larvae.

The PPAE, which is brought in contact with X-Arg-Y (see SEQ ID NO:3) in the method for assaying PPAE activity of the present invention, is subject to no limitation as long as it is PPAE per se derived from insects or contains such PPAE. A preferable example of the substance containing PPAE is body fluid of insects. The body fluid is generally hemolymph obtained from body cavity of insects, in view of easiness of obtainment.

The method for obtaining hemolymph is not limited. Preferable method includes placing an insect on an ice to bring same on halt, injecting physiological saline containing sucrose containing cane sugar factor (high molecular substance contained in sugarcane, which is composed of glucose, amino acid etc.) as an impurity, or cane sugar factor itself, into body cavity thereof, and collecting the hemolymph from the body cavity after leaving the insect for a while. The hemolymph obtained this way may be subjected to centrifugation to remove blood corpuscles and dialyzed to give blood plasma for use.

The method for assaying PPAE activity of the present invention comprises assaying a reaction product produced upon contact of PPAE present in body fluid of insects with the aforementioned peptide chain X-Arg-Y (see SEQ ID NO:3).

The detection of the reaction product can be performed by any method based on the chemical or physical properties of at least one of the reaction products X-Arg and Y.

Examples of such method include absorption measurement, colorimetry, fluorescent method (see *Zusetsu Keiko Kotai*, Soft Science Corp.), luminescence method (see *Koso Men-eki Sokuteiho: Tanpakushitsu Kakusan Koso*, extra vol. 31, pp 251–263, *Kyoritsu Shuppan* Corp.), RIA method (see *Ikagaku Jikken Koza*, vol. 8, *Nakayama Shoten*), EIA method (see *Koso Men-eki Sokuteiho:Tanpakushitsu Kakusan Koso*, extra vol. 31, pp 51–63, *Kyoritsu Shuppan* Corp.) and nuclear magnetic resonance spectrum (see *Koso Men-eki Sokuteiho:Tanpakushitsu Kakusan Koso*, extra vol. 31, pp 264–271, *Kyoritsu Shuppan* Corp.).

Specifically, the following method is exemplified.

When Y is a color developing group such as a p-nitroanilino group, changes in absorbance (absorption curve) of the system before and after the reaction can be measured by conventional methods and when Y is a fluorescent group such as a β-naphthylamino group, changes in fluorescence intensity of the system before and after the reaction can be measured by conventional methods. When Y is an organic residue labeled with an isotope such as $^{14}C$ or $^{3}H$, the presence of Y can be measured by a detection according to the kind of isotope used, after separation by liquid chromatography or electrophoresis based on the different properties such as molecular weights, hydrophobicity and hydrophilicity of X-Arg and Y. When Y is an organic residue having magneticity, measurement is done based on the release of X-Arg from X-Arg-Y (see SEQ ID NO:3) which can be immobilized on a solid carrier by the action of magnetic power.

Even if Y does not show detection specificity such as fluorescence, it can be detected by measuring absorbance after separating X-Arg and Y by liquid chromatography or electrophoresis based on the different properties such as molecular weight, hydrophobicity etc. When X-Arg has specific properties with respect to color development, fluorescence, light emission, radioactivity etc., it is also possible to measure the amount of X-Arg produced or the residual amount of X-Arg-Y (see SEQ ID NO:3) by a detection method suitably selected depending on the property it possesses.

When X is labeled with an enzyme, PPAE activity can be assayed by measuring substrate changes which are caused by bringing X-Arg or X-Arg-Y (see SEQ ID NO:3) into contact with a substance capable of acting as a substrate for the labeling enzyme. With X labeled with peroxidase, for example, the use of 5-aminosalicylic acid or o-phenylenediamine as a substrate will make the measurement of changes in absorbance (colorimetry) preferable; the use of 3-(p-hydroxyphenyl)propionic acid will make fluorescent method preferable; and the use of luminol will make light emission method preferable. With X labeled with alkaliphosphatase, moreover, the use of p-nitrophenyl phosphoric acid as a substrate will make colorimetry preferable, the use of 4-methylumbellipheryl phosphoric acid will make fluorescent method preferable; and the use of 4-methoxy-4-(3-phosphatephenyl)spiro[1,2-dioxetan-3,2'-adamantan]disodium salt (AMPPD) will make light emitting method preferable.

The method for assaying β-1,3-glucan and/or peptidoglycan of the present invention [Assay (2)] comprises the use, as an index, of the PPAE activity determined by assaying at least X-Arg or Y produced upon contact of proPO activating system and β-1,3-glucan and/or peptidoglycan, with a peptide chain of the aforementioned formula (I).

That is, Assay (2) utilizes the aforementioned Assay (1) for detecting PPAE activity to be used as an index, wherein β-1,3-glucan and/or peptidoglycan are/is assayed by using, as an index, PPAE activity which is induced by proPO activating system activated by the existence of β-1,3-glucan and/or peptidoglycan.

The proPO activating system contains a component which specifically recognizes β-1,3-glucan and/or a component which specifically recognizes peptidoglycan. In the proPO activating system, the chain of reaction is triggered by the presence of β-1,3-glucan and/or peptidoglycan to ultimately activate, by the action of a series of enzymes, at least three precursors, i.e. proBAEEase (precursor of an enzyme having an activity of hydrolyzing benzoylarginine ethyl ester), proPPAE (precursor of serineprotease which activates proPO), and proPO the system being a cascade.

The proPO activating system to be used in Assay (2) of the present invention may be or may contain the proPO activating system. Preferable example of the substance containing proPO activating system is body fluid of insects.

The body fluid of insects is exemplified by hemolymph obtained from body cavity of insects, as mentioned above. The method for obtaining the hemolymph and the kind of insects to be used are as described in the foregoing.

The β-1,3-glucan, which is the determination target in the present invention, includes, for example, but not limited to, glucose polymers or derivatives thereof having β-1,3-bond, such as zymosan, curdlan, pachyman, sclerotan, lentinan, schizophyllan, choriolan, laminaran, lichenan and derivatives thereof.

The peptidoglycan, which is also the determination target in the present invention, is not specifically limited and is exemplified by components constituting cell walls of various bacteria such as those belonging to the genus Micrococcus, the genus Streptococcus, the genus Aureobacterium, the genus Bacillus and the genus Agrobacterium.

Assay (2) of the present invention aims at specifically detecting and quantitatively assaying β-1,3-glucan and/or peptidoglycan. According to this method, it is possible to identify a sample containing β-1,3-glucan and/or peptidoglycan, or quantitatively determine β-1,3-glucan and/or peptidoglyean in the sample.

Assay (2) aims at determining PPAE activity in a reaction mixture by measuring, according to the aforementioned Assay (1), X-Arg or Y, which has been produced in a solution composed of a sample possibly containing β-1,3-glucan and/or peptidoglycan, a solution containing the peptide chain of the formula (I) and a solution containing proPO activating system, preferably body fluid of insects, after a certain period of time allowed for reaction.

The peptide chain used only needs to have a detectable concentration and is prepared as appropriate according to the assay system. The amount of the proPO activating system only needs to be an amount permitting action of the proPO cascade, which is appropriately adjusted according to the assay method.

The reaction pH is generally 4–11, preferably 6–9. A buffer may be used to maintain said pH and such buffer is subject to no particular limitation in terms of kind and concentration, insofar as it does not exert adverse influence on the reaction. Examples thereof include phosphate buffer, borate buffer, acetate buffer, Tris buffer and Good's buffer.

The reaction temperature and reaction time, too, are not subject to any limitation insofar as they permit progress of the reaction. The reaction temperature is generally 0°–50° C., preferably 4°–30° C. The reaction time is generally from 1 second to 20 hours, preferably from 10 seconds to 2 hours.

It is preferable that 0.001–1000 mM, preferably 5–100 mM bivalent metal ion such as $Ca^{2+}$ or $Mg^{2+}$ should be present in the assay system of the present invention.

When β-1,3-glucan and peptidoglycan are present in a sample to be assayed by Assay (2) for β-1,3-glucan and/or peptidoglycan, the obtained PPAE activity is expressed by the total of β-1,3-glucan and peptidoglycan.

Assay (3) of the present invention specifically detects and quantitatively determines β-1,3-glucan and Assay (4) of the present invention specifically detects and quantitatively determines peptidoglycan.

Assay (3) for β-1,3-glucan is the aforementioned Assay (2) wherein used is the proPO activating system which has undergone removal of a component that specifically reacts with peptidoglycan. The component which specifically reacts with peptidoglycan is, for example, peptidoglycan recognition protein.

Assay (4) for peptidoglycan is the aforementioned Assay (2) wherein used is the proPO activating system which has undergone removal of a component that specifically reacts with β-1,3-glucan. The component which specifically reacts with β-1,3-glucan is, for example, β-1,3-glucan recognition protein.

The method for removing a component which specifically reacts with peptidoglycan or β-1,3-glucan from the proPO activating system includes separation and purification generally used in the field of biochemistry, such as gel filtration, electrophoresis, affinity chromatography, ion exchange chromatography and centrifugation. As a method for removing a component which specifically reacts with peptidoglycan, exemplified is affinity chromatography wherein a carrier bound with peptidoglycan is used (U.S. Pat. No. 4,970,152) and as a method for removing a component which specifically reacts with β-1,3-glucan, exemplified is affinity chromatography wherein a carrier bound with β-1,3-glucan is used (U.S. Pat. No. 4,970,152).

According to the present invention, PPAE activity can be quantitatively assayed with precision and a highly precise method for determining β-1,3-glucan and/or peptidoglycan, wherein said PPAE activity is used as an index, can be provided.

In addition, the present invention enables detection of fungi and bacteria without multiplication by culture, which makes early diagnosis of microbial infections possible. The present invention is applicable to a wide range of use such as tests for microbial contamination of water and food, safety tests of therapeutic agents such as antibiotics and injectable preparations, etc.

The present invention is more detailedly described in the following by illustrating Examples and Reference Examples, which do not limit the present invention in any way.

REFERENCE EXAMPLE 1

Identification of amino acid sequence of PPAE recognition-cleavage site on proPO from sericulture silkworm (1) Purification of proPO from sericulture silkworm larvae Saturated ammonium sulfate (pH 6.5) was added to about 200 ml of hemolymph obtained from 5 instar sericulture silkworm larvae to give a 70% ammonium sulfate solution and the solution was left standing overnight at 4° C. Thereto was added 0.2M potassium phosphate buffer (pH 6.5) to give a 40% ammonium sulfate solution. The solution was gently stirred for 2 hours and left standing, followed by centrifugation at 8000 rpm for 20 min (Hitachi RPR 9-2 rotator, hereinafter the same) to give a supernatant. Then, saturated ammonium sulfate (pH 6.5) was added to the supernatant to give a 50% ammonium sulfate solution and the solution was left standing overnight. The solution was subjected to centrifugation at 8000 rpm for 20 min to allow precipitation. The precipitate was dissolved in 0.1M potassium phosphate buffer (pH 6.5)-20% ammonium sulfate solution (pH 6.5) and saturated ammonium sulfate (pH 6.5) was further added thereto to give a 38% ammonium sulfate solution. The mixture was stirred for 1 hour, left standing for 2.5 hours and centrifuged at 10000 rpm for 20 min to give a supernatant. Saturated ammonium sulfate (pH 6.5) was added thereto to give a 48% ammonium sulfate solution. The mixture was stirred for 30 min, left standing overnight and centrifuged at 8000 rpm for 20 min to allow precipitation. The precipitate was dissolved in 0.01M potassium phosphate buffer and dialyzed against the same buffer.

The sample which had undergone dialysis was centrifuged at 12000 rpm for 20 min and the obtained supernatant was warmed to 54.5° C. in a water bath at 65° C. with stirring, followed by 5 more minutes of warming in a water bath at 55° C. After rapidly cooling with ice, the sample was centrifuged at 18000 rpm for 20 minutes to give a supernatant.

The supernatant was subjected to DEAE cellulose column chromatography (manufactured by Wako Pure Chemical Industries, Ltd., Japan, φ1.5×19 cm) and eluted with the gradient of KCl for fractionation. Each fraction was examined for possible PO activity which developed after activation with crude PPAE, whereby proPO fractions were recovered. The obtained proPO fraction was dialyzed against 0.04M KCl-0.01M potassium phosphate buffer (pH 6.0).

The sample was subjected to hydroxyapatite column chromatography (manufactured by Wako Pure Chemical Industries, Ltd., Japan, φ1.5×9.3 cm) and eluted with 50 mM, 75 mM or 95 mM potassium phosphate buffer (pH 6.0). The PO activity in the obtained fractions was assayed by the aforementioned method. As a result, elution of proPO was confirmed in the 50 mM potassium phosphate buffer (pH 6.0) and the fractions thereof were recovered.

The fractions were concentrated in Collodion Bag (SM13200) of Sartrius Corp. and dialyzed against 0.01M Tris-HCl buffer (pH 7.75) to give a purified proPO solution.

(2) Purification of PPAE

A homogenate of the cuticles of 5 instar sericulture silkworm larvae was fractionated with ammonium sulfate and 0.2–0.4% ammonium sulfate fractions were recovered. The fractions were dialyzed against 0.01M Tris-HCl-0.01M CaCl$_2$ buffer (pH 8.5) and then against 0.01M Tris-HCl buffer (pH 8.5). The dialyzed solution was poured on DEAE cellulose column and eluted with 0.01M Tris-HCl buffer (pH 8.5). The fractions showing PPAE activity were recovered and applied to hydroxyapatite column. The obtained fractions were washed with 0.01M potassium phosphate buffer (pH 7.5) and eluted with a linear gradient of potassium phosphate buffer (pH 7.5) from 0.01M to 0.5M. The fractions showing PPAE activity were recovered and used as a purified PPAE solution.

(3) Analysis of amino acid sequence of peptide fragment obtained by cleaving proPO with PPAE The above-mentioned purified proPO was incubated with purified PPAE. The reaction mixture was applied to Sephadex G-50 column, eluted with 0.01M potassium phosphate buffer (pH 8.0) and peptide chains cleaved and released from proPO were recovered. The peptide chains were divided into three fragments (fI, fII, fIII) by ODS column. The fragments were fragmented by treating with Lys-endopeptidase and the amino acid sequences thereof were examined by Edman degradation. As a result, it was found that fI and fII had the same sequence (see SEQ ID NO:11), though with slight modifications, and fIII had a different sequence (see SEQ ID NO:10).

(4) Analysis of amino acid sequence of N-terminal of PO produced by cleaving the aforementioned peptide from proPO with PPAE The proPO in 0.01M potassium phosphate buffer (pH 7.5), thiourea and PPAE in 75 mM potassium phosphate (pH 7.5) were incubated at 0° C. for 3 hours to convert the entire proPO to PO. The reaction mixture was divided into two major fractions by ODS column and the amino acid sequence of each N-terminal was identified by Edman degradation (see SEQ ID NOS: 7 and 8).

REFERENCE EXAMPLE 2

Identification of DNA base sequence of PPAE recognition-cleavage site on silkworm proPO (1) Construction of sericulture silkworm cDNA library The body fluid (25 ml) was obtained from five hundred 5 instar sericulture silkworm larvae and centrifuged (40 G, 15 min, 4° C.) to separate blood corpuscle cells. About 800 µg of total RNA was prepared therefrom with the use of RNA extraction kit ISOGEN (manufactured by Wako Pure Chemical Industries, Ltd., Japan).

mRNA was prepared from the total RNA with the use of mRNA Purification Kit (Pharmacia) and cDNA was synthesized using cDNA Synthesis Kit (Pharmacia). The synthesized cDNA was cloned into EcoRI site of λZAPII phage vector and subjected to in vitro packaging with the use of Gigapack Gold packaging extract (Stratagene). As a result, there was obtained phage library of $4.2 \times 10^5$ plaque forming unit (PFU).

(2) Screening of proPO clones

The screening was done with the use of PicoBlue™ Immunoscreening Kit (Stratagene).

The sericulture silkworm cDNA phage library ($1.5 \times 10^4$ PFU) was mixed with 200 µl of E. coli XL-1 Blue ($OD_{600}$=about 0.5) and the mixture was incubated at 37° C. for 15 minutes, which was then sown in an NZY plate (1.5% agar, 1% NZ amine, 0.2% $MgSO_4 \cdot 7H_2O$, 0.5% bactoyeast extract, 0.5% NaCl, 12.5 µg/ml tetracycline, pH 7.5) and cultured at 42° C. for about 3.5 hours. When plaques emerged, a nitrocellulose filter (Amarsham) impregnated with 10 mM IPTG (isopropylthiogalactoside) was placed thereon and cultured at 37° C. for 3.5 hours. Then, the nitrocellulose filter was carefully removed with a tweezer and washed 3–5 times with TBST [20 mm Tris-HCl (pH 7.5), 150 mM NaCl, 0.05% (V/V) Tween 20] for 15 minutes.

So as to prepare two replica filters to be screened per plate, another nitrocellulose filter impregnated with 10 mM IPTG was placed on the plate upon removal of the first filter and incubated at 37° C. for 4 hours. The second filter was washed in the same manner as with the first filter.

This operation was done for 20 plates to prepare replica filters having $3.0 \times 10^5$ plaques in total.

These filters were gently shaken in a blocking solution [1% BSA, 20 mM Tris-HCl (pH 7.5), 150 mm NaCl] for 1 hour, transferred to an anti-proPO rabbit antibody solution appropriately diluted with the blocking solution and gently shaken at room temperature for 1 hour. The replica filters which underwent primary reaction were washed 3–5 times with TBST for 5 min per washing and gently shaken in an alkaliphosphatase-labeled anti-rabbit IgG goat antibody solution appropriately diluted with the blocking solution, at room temperature for 1 hour for secondary reaction. After the reaction, the mixture was washed 3–5 times with TBST for 5 min and with TBS [20 mm Tris-HCl (pH 7.5), 150 mM NaCl, 1% BSA] for 5 min. The waterdrops on the replica filters were suctioned with a filter and the filters were allowed to develop color in a color developing solution [0.3 mg/ml nitroblue tetrazolium, 0.15 mg/ml 5-bromo-4-chloro-3-indolylphosphate, 100 mM Tris-HCl (pH 9.5), 100 mM NaCl, 5 mM $MgCl_2$].

The plaques corresponding to the position of blue on the nitrocellulose filter were picked from the plate and subjected to secondary screening and tertiary screening for purification, whereby 8 clones were ultimately obtained.

(3) Subcloning

The DNA fragment cloned into λZAPII was automatically cleaved therefrom by the action of a helper phage and cyclized again. Accordingly, the following operation was done to allow subcloning in a pBluescript SK(-) phagemid vector.

λZAPII recombinant phage (100 µl, >$1 \times 10^5$ PFU), E. coli XL-1 Blue (200 µl, $OD_{600}$=about 1.0) and ExAssist helper Phage (1 µl, >$1 \times 10^6$ PFU) were mixed and incubated at 37° C. for 15 minutes. Thereto was added 3 ml of 2×YT medium (1% NaCl, 1% yeast extract, 1.6% bactotrypton) and the mixture was shake-cultured for 2.5 hours, followed by incubation at 70° C. for 20 min. The mixture was centrifuged (4000×g, 15 min, room temperature) to give a supernatant. An aliquot (1 µl) thereof was mixed with 200 µl of E. coli SOLR™ ($OD_{600}$=about 1.0), and the mixture was incubated at 37° C. for 15 minutes and plated on an LB/Amp plate (1.5% agar, 1% NaCl, 1.6% bactotrypton, 0.5% yeast extract, 50 µg/ml ampicillin). Single colonies (pPO2, pPO3, pPO4, pPO5, pPO6, pPO8, pPO17, pPO20) were selected.

(4) Identification of base sequence of proPO clones

A restriction enzyme cleavage map was depicted with respect to the subcloned clones. pPO2, pPO3, pPO4, pPO8, pPO17 and pPO20 were considered to clone the same protein, in view of the similar restriction enzyme site, and pPO17 was selected as a representative. In addition, it was considered that pPO5 and pPO6 cloned different proteins and that pPO6 was a partial clone of pPO2 etc. Accordingly, pPO5 was selected as another candidate.

For possible cleavage on proPO by PPAE, the base sequences of 5' side of the cDNA insertion fragments putatively including the cleavage site, with respect to pPO5 and pPO17, were identified. The base sequence was identified using Taq DyeDeoxy™ Terminator Cycle Sequencing Kit (Applied Biosystems Corp.) using AmpliTaq® DNA polymerase, with recombinant plasmid DNA as a template, followed by analysis by ABI 373A DNA sequencer. The thus-obtained sequences (see SEQ ID NO: 12 and 13) were checked against the amino acid sequence of Reference Example 1. The combination of the peptides obtained in Reference Example 1 was decided and the amino acid sequence of the region on the proPO, where PPAE recognizes and cleaves, was identified. Said amino acid sequence and the codons corresponding thereto are shown as Sequence Nos. 5 and 6 in the Sequence Listing given below.

As is evident from these sequences, the two clones pPO5 and pPO17 have different sequences, suggesting that proPO proteins recognized and cleaved by PPAE are two.

EXAMPLE 1

Assay of PPAE activity (1) Synthesis of peptide

A peptide having the sequence

2-Pyr-Ala-Leu-Asn-Arg-Phe-Gly-OH (see SEQ ID NO:2)

wherein 2-Pyr is 2-pyridyl, was synthesized by a peptide synthesizer (PSSM-8 type, manufactured by Shimadzu Corporation) with the use of Fmoc-Gly-Alko resin (manufactured by Watanabe Kagaku Kogyo).

Peptide synthesis was performed by treating an Fmoc group (9-fluorenylmethoxycarbonyl) of Fmoc-Gly-Alko resin with 30% piperidine in DMF to release terminal amino, and sequentially condensing Fmoc-Phe, Fmoc-Arg, Fmoc-Asn, Fmoc-Asn, Fmoc-Leu and 2-Pyr-Ala for introducing 2-pyridylamino in the presence of a BOP reagent.

The resin to which the thus obtained peptide chain had bound was washed with methanol and dried. Then, the resin was immersed in a solution of trifluoroacetic acid (950 µl) and thioanisole (50 µl) for 1 hour to release the peptide. The peptide was washed with trifluoroacetic acid and the filtrate was recovered. Anhydrous ethyl ether was added to the filtrate and the resulting white precipitate was centrifuged (2000 rpm, 6 min, 4° C.) and dried under reduced pressure. For further purification, the white precipitate was dissolved in 30% acetic acid and applied to 5C18 reversed phase chromato column (manufactured by Wako Pure Chemical Industries, Ltd., Japan) to obtain main fraction which was lyophilized. Immediately before use, the fraction was dissolved in 0.01M potassium phosphate buffer (pH 7.0) and used as a synthetic peptide solution.

(2) Purification of PPAE

The cuticles (about 100 g) of about five hundred 5 instar sericulture silkworm larvae were obtained and washed with cool distilled water, followed by homogenization. The obtained homogenate was subjected to ammonium sulfate fractionation according to the reaction scheme of FIG. 1.

The possible PPAE activity in each ammonium sulfate fraction was examined by observing the development of PO activity as a result of the action of PPAE on proPO as a substrate. In order to confirm that the PO activity was derived from the proPO added, the PO activity of the same fraction without proPO was also examined. These PO activities were determined by using DOPA as a substrate and measuring absorbance at OD490 nm due to the color development by dopachrome produced.

As a result, PPAE activity (development of PO activity) was found in supernatant 1, precipitate 2, supernatant 3 and precipitate 4 (see FIG. 1), whereas PO activity originally present was found in supernatant 1 and precipitate 2 to a considerable degree and in supernatant 3 to some degree. Accordingly, precipitate 4 was considered to be a PPAE fraction. The fraction was dialyzed against 0.01M Tris-HCl buffer (pH 8.5) and used as a PPAE solution.

(3) Assay of PPAE activity by liquid chromatography

A synthetic peptide solution (50 µl) dissolved in 0.01M potassium phosphate buffer (pH 7.0) at a suitable concentration was mixed with PPAE solution (50 µl) dissolved in 0.01M Tris-HCl buffer (pH 8.5) at a concentration of 0.36 mg/ml and the mixture was heated at 30° C. for 10 minutes. An aliquot (10 µl) thereof was analyzed by liquid chromatography [column: Wakosil-5C18 (4.6 i.d.×250 mm, manufactured by Wako Pure Chemical Industries, Ltd., Japan); column temperature: 40° C.; mobile phase: A buffer (50 mM AcONH$_4$ (pH 6.0)-10% acetonitrile); B buffer (50 mM AcONH$_4$ (pH 6.0)-50% acetonitrile); gradient: B buffer 0→50% (0→15 min); flow rate: 1.5 ml/min; detection: Ex 305 nm, Em 376 nm] (FIG. 2-A). As controls, a mixture of the aforementioned synthetic peptide solution (50 µl) and 0.01M Tris-HCl buffer (50 µl, pH 8.5) (FIG. 2-B) and a mixture of 0.01M potassium phosphate buffer (50 µl, pH 7.0) and the aforementioned PPAE solution (50 µl) (FIG. 2-C) were treated in the same manner and subjected to liquid chromatography. As a result, cleaved fractions of the synthetic peptide were confirmed. That is, a peak indicating the cleaved fraction of the synthetic peptide emerged at retention time 7,225 min in the liquid chromatography analysis of FIG. 2-A, and PPAE activity was determinable.

(4) Correlation between PPAE concentration and activity

Figure 3:
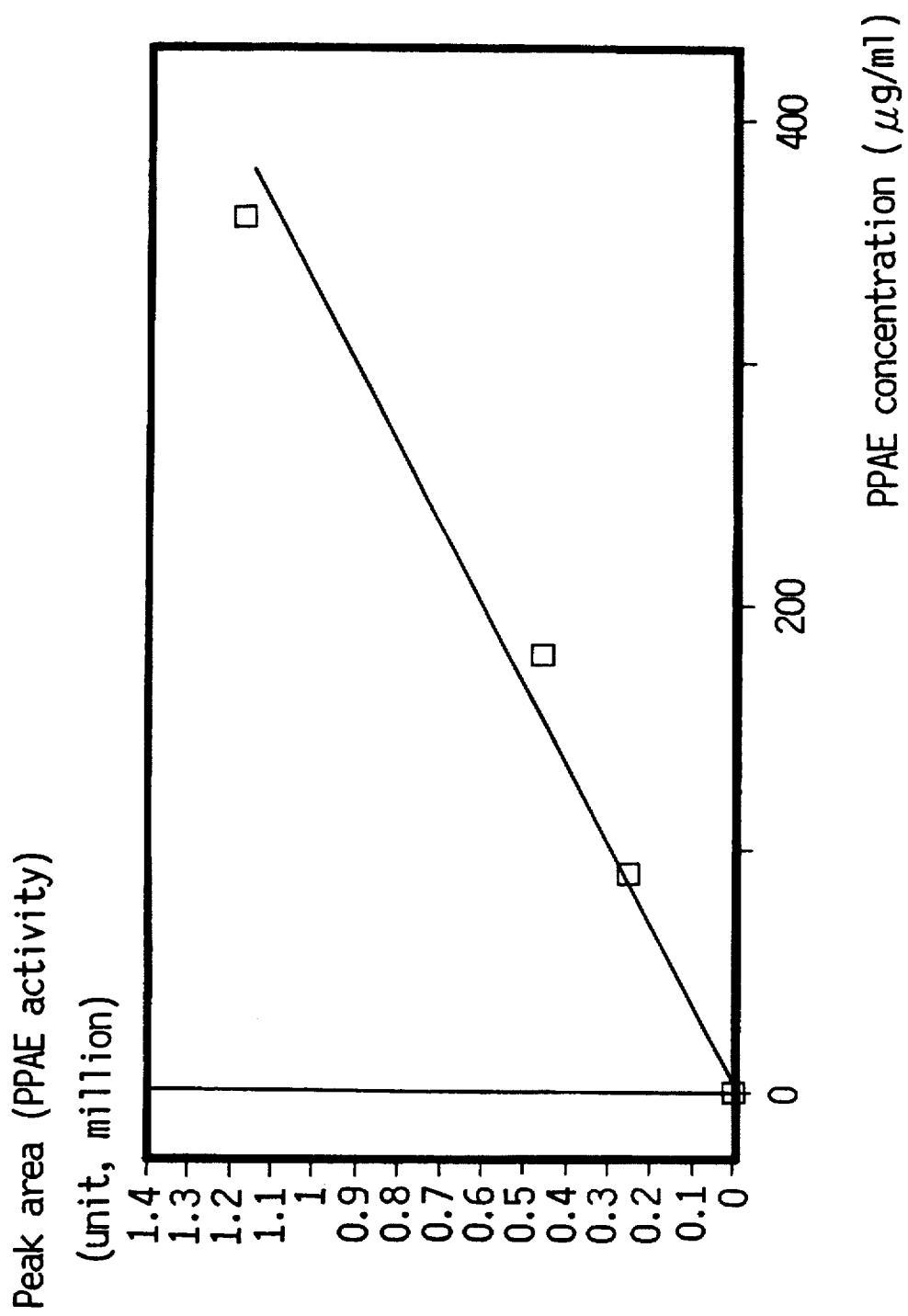
FIG. 3 is a graph showing the correlation between PPAE concentration and PPAE activity.

A synthetic peptide solution (50 µl) dissolved in 0.01M potassium phosphate buffer (pH 7.0) at a suitable concentration was mixed with PPAE solution (50 µl) dissolved in 0.01M Tris-HCl buffer (pH 8.5) at a concentration of 0, 0.18, 0.36 or 0.72 mg/ml and the mixture was heated at 30° C. for 5 minutes. An aliquot (10 µl) thereof was analyzed by liquid chromatography. The peak area of the cleaved fraction of the synthetic peptide was taken as PPAE activity value and the correlation between the activity and PPAE concentration was examined. As a result, a clear correlation was confirmed (FIG. 3), enabling quantitative assay of PPAE activity using the peptide.

REFERENCE EXAMPLE 3

Preparation of SLP solution

Sericulture silkworm (*Bombyx mori*) larvae (5 instar) were placed on ice for 10 minutes to stop movement thereof and a 20 mM solution of sucrose purified from sugarcane was injected from between the fifth abdominal node and the sixth abdominal node in an amount weighing half the body weight of a larva. The larvae were tied at before the fifth abdominal node with a sewing thread so as to keep the injected solution inside the larvae and left at room temperature for 20 minutes. Then, the limb at the third abdominal node was cut to recover hemolymph therefrom.

The recovered hemolymph was centrifuged at low temperature and at 1500 G for 5 min to remove blood corpuscle. The obtained supernatant (ca. 100 ml) was dialyzed against a solution (3 l) of 0.1 mM MOPS [3-(N-morpholino)propanesulfonic acid], 0.1M KCl and 1% xylitol at low temperature for 2 days to give an SLP solution.

EXAMPLE 2

Figure 4:
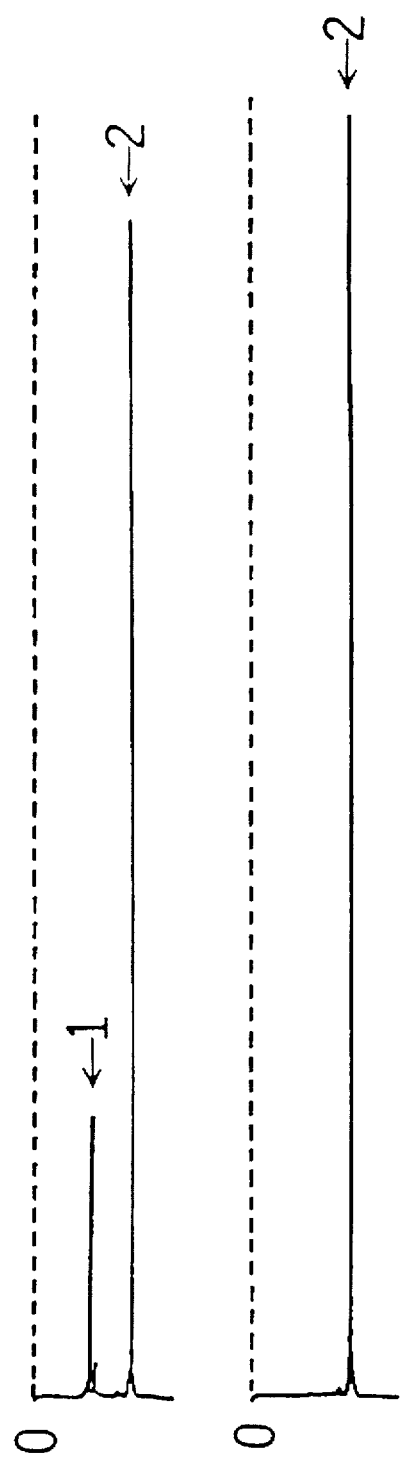
FIGS. 4A and 4B is a liquid chromatogram showing the detection of CM-curdlan by the use of a synthetic peptide as a substrate, wherein 1 is a peak of the reaction product (2-Pyr-Ala-Leu-Asn-Arg-OH) (see SEQ ID NO:1) and 2 is a peak of the synthetic peptide (2-Pyr-Ala-Leu-Asn-Arg-Phe-Gly-OH) (see SEQ ID NO:2).

Assay of β-1,3-glucan (1) Assay of β-1,3-glucan using hemolymph (SLP) of sericulture silkworm larvae As typical β-1,3-glucan, used was carboxymethyl curdlan (CM-curdlan). The synthetic peptide solution (10 µl) obtained in Example 1 (1) and dissolved in 0.01M potassium phosphate buffer (pH 7.0) at a suitable concentration, an SLP solution (5 µl) dissolved in 0.1M MOPS [3-(N-morpholino)propanesulfonic acid], 0.1M KCl and 1% xylitol, 10 mM phenylthiourea (10 µl), 80 mM CaCl$_2$ (15 µl), 1 mg/ml CM-curdlan (5 µl), 0.01M Tris-HCl buffer (100 µl, pH 8.5) and distilled water (55 µl) were mixed and the mixture was heated at 25° C. for 25 minutes. An aliquot (10 µl) thereof was analyzed by liquid chromatography [column: Wakosil-SC18 (4.6×250 mm) manufactured by Wako Pure Chemical Industries, Ltd., Japan); column temperature: 40° C.; mobile phase: A buffer (50 mM AcONH$_4$ (pH 6.0)-10% acetonitrile); B buffer (50 mM AcONH$_4$ (pH 6.0)-50% acetonitrile); gradient: B buffer 0→50% (0→15 min); flow rate: 1.5 ml/min; detection: Ex 305 nm, Era 376 nm] (FIG. 4-A). As a control, a mixture of the aforementioned composition except that 5 µl of distilled water was additionally added in place of 1 mg/ml CM-curdlan (FIG. 4-B) was treated in the same manner and subjected to liquid chromatography. As a result, a peak indicating the cleaved fraction of the synthetic peptide emerged at retention time 6.279 min and β-1,3-glucan was detected. The SLP solution used was prepared by the method described in Reference Example 3.

(2) Correlation between β-1,3-glucan concentration and activity

As typical β-1,3-glucan, used was CM-curdlan.

Figure 5:
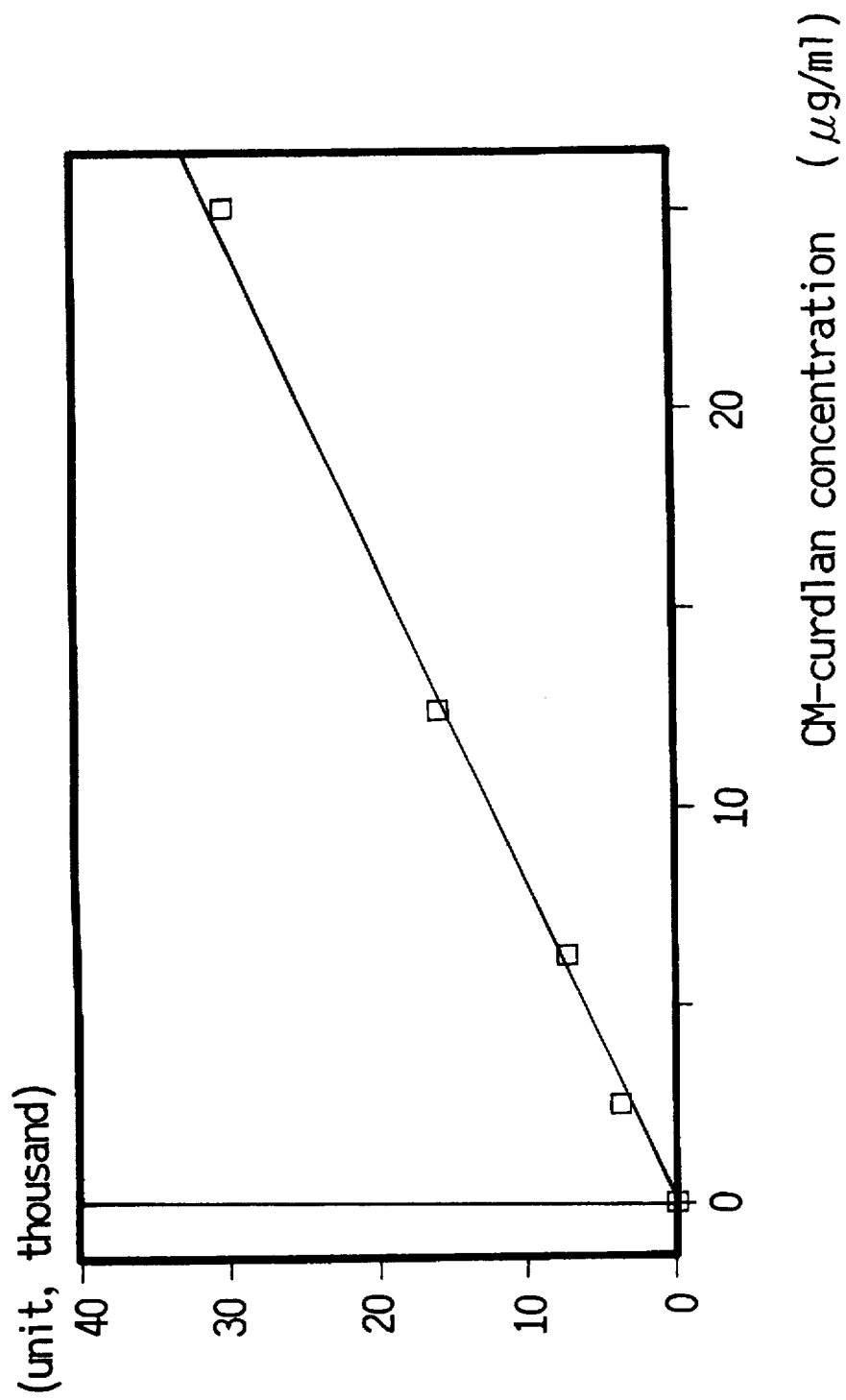
FIG. 5 is a graph showing the correlation between CM-curdlan concentration and PPAE activity.

CM-Curdlan (5 µl) at a concentration of 0, 0.1, 0.25, 0.5 or 1.0 mg/ml was added to a mixture of a synthetic peptide solution (10 µl) dissolved in 0.01M potassium phosphate buffer (pH 7.0) at a suitable concentration, an SLP solution (5 µl) dissolved in 0.1M MOPS, 0.1M KCl and 1% xylitol, 10 mM phenylthiourea (10 µl), 80 mM CaCl$_2$ (15 µl), 0.01M Tris-HCl buffer (100 µl, pH 8.5) and distilled water (55 µl), and the mixture was heated at 25° C. for 25 minutes. An aliquot (10 µl) thereof was analyzed by liquid chromatography. The peak area of the cleaved fraction of the synthetic peptide was taken as PPAE activity value and the correlation between the activity and concentration of CM-curdlan was examined. As a result, a clear correlation was confirmed (FIG. 5), enabling quantitative assay of β-1,3-glucan using said peptide.

EXAMPLE 3

Assay of peptidoglycan using body fluid (SLP) of sericulture silkworm larvae

The peptidoglycan prepared by ultrasonic rupture of *Micrococcus lysodeikticus* (IFO3333) was used as typical peptidoglycan in the following tests.

An SLP solution (80 µl) dissolved in 0.1M MOPS, 0.1M KCl and 1% xylitol, 80 mM CaCl$_2$ (7.5 µl), 0.3 mg/ml peptidoglyean solution (10 µl) and distilled water (2.5 µl) were mixed and the mixture was heated at 30° C. for 10 minutes. Thereto were sequentially added and mixed 0.5M EDTA (5 µl), 1M Tris-HCl buffer (5 µl, pH 8.5) and a synthetic peptide solution (10 µl) prepared in Example 1 (1) and adjusted to a suitable concentration. The mixture was heated at 30° C. for 30 minutes. After the reaction, 50 µl therefrom was analyzed by liquid chromatography (analysis conditions were the same as those for the analysis of β-1,3-glucan in Example 2) (FIG. 6-A). As a control, a mixture of the aforementioned composition except that 10 µl of distilled water was additionally added in place of 0.3 mg/ml peptidoglycan solution (FIG. 6-B) was treated in the same manner and subjected to liquid chromatography. As a result, a peak indicating the cleaved fraction of the synthetic peptide emerged at retention time 4.36 min only when peptidoglycan was added (FIG. 6-A), enabling assay of peptidoglycan using the synthetic peptide. The SLP solution used was prepared by the method described in Reference Example 3.

REFERENCE EXAMPLE 4

Substrate specificity of PPAE

Four kinds of peptide chains Ala-Leu-Asn-*-Arg-Phe-Gly (see SEQ ID NO:9) wherein * is Asn, Asp, Ser or Gly, with 2-pyridyl introduced at the N-terminal were synthesized and dissolved in distilled water to the concentration of 0.5 mg/ml. To these solutions (125 µl each) were added 10 µg/ml PPAE (25 µl), 1M Tris-HCl buffer (25 µl, pH 8.5), 5M NaCl (25 µl) and distilled water (50 µl ), and the mixture was reacted at 25° C. for 0, 15 or 30 minutes. At every reaction, 80 µl of the reaction mixture was taken out and 50% acetic acid (20 µl) was added thereto to terminate the reaction. Distilled water (100 µl) was added thereto and mixed. An aliquot (100 µl) thereof was analyzed by liquid chromatography. The percentage of reduction per 15 min of the peak area indicating the synthetic peptide Ala-Leu-Asn-*-Arg-Phe-Gly (see SEQ ID NO:9) found by the analysis was calculated and taken as percent substrate reduction. The four peptides were compared in terms of the obtained percent reduction. The results are shown in Table 1.

TABLE 1

| | Substrate: Ala—Leu—Asn—*—Arg—Phe—Gly (SEE SEQ ID NO:9) | |
|---|---|---|
| Amino acid for * | Substrate reduction (%) (15 min reaction) | Apparent reaction rate (nmole/µg PPAE/min) |
| Asn | 27.7 | 2.05 |
| Asp | 26.6 | 1.96 |
| Ser | 10.3 | 0.77 |
| Gly | 2.3 | 0.18 |

As is evident from Table 1, percent substrate reduction was less and PPAE reaction rate became smaller when the amino acid for * was Gly.

As a result, when the amino acid for * is Gly, the peptide is not suitable for use as a substrate for the assay of PPAE activity.

What is claimed is:

1. A method for assaying an activity of a prophenoloxidase activating enzyme, which comprises, (1) reacting a prophenoloxidase activating enzyme with a peptide chain represented by formula (I)

$$X\text{-Arg-}Y \qquad (I)$$

wherein

X is an optionally labelled amino acid residue having an optionally protected α-amino group, or an optionally labelled peptide residue consisting of 2 to 20 amino acids, having an optionally protected N-terminal, provided that the amino acid residue adjoining Arg is not Gly or Ala, and Y is an organic residue capable of binding to a carboxyl group of Arg by acid amide bonding or ester bonding, or an optionally labelled amino acid residue having an optionally protected α-carboxyl group, or an optionally labelled peptide residue consisting of 2 to 20 amino acids, having an optionally protected C-terminal, the peptide chain being hydrolyzable into X-Arg and Y by a prophenoloxidase activating enzyme derived from an insect, (2) measuring the amount of at least one of X-Arg and Y produced by the reaction between the peptide chain represented by the formula (I) and the prophenoloxidase activating enzyme, and (3) determining the prophenoloxidase activating enzyme activity on the basis for the amount measured in (2).

2. A method according to claim 1, wherein X is a group represented by the formula $$X'\text{-Asn}$$

wherein X' is an optionally labeled amino acid residue having an optionally protected α-amino group, or an optionally labeled peptide residue having an optionally protected N-terminal, with the proviso that X' has amino acids of the same number as X has less 1, or a protecting group for an α-amino group of Asn.

3. A method according to claim 1 or claim 2, wherein Y is a group represented by the formula $$\text{Phe-Gly-}Z$$

wherein Z is an optionally labeled amino acid residue having an optionally protected α-carboxyl group, or an optionally labeled peptide residue having an optionally protected C-terminal, with the proviso that Z has amino acids of the same number as Y has less 2, or a protecting group for a carboxyl group of Gly.

4. A method according to any one of claim 1 to claim 3, wherein the amount of at least one of X-Arg and Y is measured by a method based on ultraviolet or visible light absorbance, luminescence, fluorescence, radioactivity or magneticity, according to the property of X-Arg or Y.

5. A method for assaying at least one of β-1,3-glucan and peptidoglycan in a sample, which comprises, (1) providing a sample containing a prophenoloxidase activating system;

(2) bringing the prophenoloxidase activating system into contact with the sample suspected of containing at least one of β-1,3-glucan and peptidoglycan, and a peptide chain represented by the formula (I)

$$X\text{-Arg-}Y \qquad (I)$$

wherein

X is an optionally labeled amino acid residue having an optionally protected α-amino group, or an optionally labeled peptide residue consisting of 2 to 20 amino acids, having an optionally protected N-terminal, provided that the amino acid residue adjoining Arg is not Gly or Ala, and Y is an organic residue capable of binding to a carboxyl group of Arg by acid amide bonding or ester bonding, or an optionally labeled amino acid residue having an optionally protected α-carboxyl group, or an optionally labeled peptide residue consisting of 2 to 20 amino acids having an optionally protected C-terminal, the peptide chain being hydrolyzable into X-Arg and Y by a prophenoloxidase activating enzyme derived from an insect;

(3) measuring the amount of at least one of X-Arg and Y produced upon contact of the peptide chain described by the formula (I) with the prophenoloxidase activating system and at least one of β-1,3-glucan and peptidoglycan;

(4) determining the prophenoloxidase activating enzyme activity by the amount of at least one of X-Arg and Y produced; and (5) determining the amount of at least one of β-1,3-glucan and peptidoglycan present from the prophenoloxidase activating enzyme activity determined in (4).

6. A method according to claim 5, wherein X is a group represented by the formula $$X'\text{-Asn}$$

wherein X' is an optionally labeled amino acid residue having an optionally protected α-amino group, or an optionally labeled peptide residue having an optionally protected N-terminal, with the proviso that X' has amino acids of the same number as X has less 1, or a protecting group for an α-amino group of Asn.

7. A method according to claim 5 or claim 6, wherein Y is a group represented by the formula Phe-Gly-Z wherein Z is an optionally labeled amino acid residue having an optionally protected α-carboxyl group, or an optionally labeled peptide residue having an optionally protected C-terminal, with the proviso that Z has amino acids of the same number as Y has less 2, or a protecting group for a carboxyl group of Gly.

8. A method according to any one of claim 5 to claim 7, wherein the amount of at least one of X-Arg and Y is measured by a method based on ultraviolet or visible light absorbance, luminescence, fluorescence, radioactivity or magneticity, according to the property of X-Arg or Y.

9. A method according to any one of claim 6 to claim 8, wherein the prophenoloxidase activating system does not comprise a component which specifically reacts with peptidoglycan.

10. A method according to any one of claim 6 to claim 8, wherein the prophenoloxidase activating system does not comprise a component which specifically reacts with β-1, 3-glucan.

* * * * *

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 4 amino acids
        ( B ) TYPE: amino acids
        ( C ) STRANDEDNESS: unknown
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:1:

Ala Leu Asn Arg
1

( 2 ) INFORMATION FOR SEQ ID NO:2:

( i ) SEQUENCE CHARACTERISTICS:
        ( A ) LENGTH: 6 amino acids
        ( B ) TYPE: amino acids
        ( C ) STRANDEDNESS: unknown
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:2:

Ala Leu Asn Arg Phe Gly
1                     5

( 2 ) INFORMATION FOR SEQ ID NO:3:

( i ) SEQUENCE CHARACTERISTICS:
        ( A ) LENGTH: 3 amino acids
        ( B ) TYPE: amino acids
        ( C ) STRANDEDNESS: unknown
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:3:

Xaa Arg Xaa
1

( 2 ) INFORMATION FOR SEQ ID NO:4:

( i ) SEQUENCE CHARACTERISTICS:
        ( A ) LENGTH: 3 amino acids
        ( B ) TYPE: amino acids
        ( C ) STRANDEDNESS: unknown
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal (vi) ORIGINAL SOURCE:

(xi) SEQUENCE DESCRIPTION: SEQ ID NO:4:

Phe Gly Xaa
1

(2) INFORMATION FOR SEQ ID NO:5:

(i) SEQUENCE CHARACTERISTICS:
  (A) LENGTH: 21 amino acids
  (B) TYPE: amino acids
  (C) STRANDEDNESS: unknown
  (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:5:

Phe Gln Leu Thr Glu Gln Phe Leu Thr Glu Asp Tyr Ala Asn Asn Gly
1               5                   10                  15
Ile Glu Leu Asn Asn
            20

(2) INFORMATION FOR SEQ ID NO:6:

(i) SEQUENCE CHARACTERISTICS:
  (A) LENGTH: 10 amino acids
  (B) TYPE: amino acids
  (C) STRANDEDNESS: unknown
  (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:6:

Tyr Gln Arg Val Ser Asn Ala Ile Gly Asn
1               5                   10

(2) INFORMATION FOR SEQ ID NO:7:

(i) SEQUENCE CHARACTERISTICS:
  (A) LENGTH: 22 amino acids
  (B) TYPE: amino acids
  (C) STRANDEDNESS: unknown
  (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:7:

Phe Gly Asp Asp Ala Ser Glu Lys Ile Pro Leu Lys Asn Leu Ser Lys
1               5                   10                  15

Leu Pro Glu Phe Lys Ile
            20

( 2 ) INFORMATION FOR SEQ ID NO:8:

( i ) SEQUENCE CHARACTERISTICS:
        ( A ) LENGTH: 10 amino acids
        ( B ) TYPE: amino acids
        ( C ) STRANDEDNESS: unknown
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:8:

Phe Gly Ser Asp Ala Gly Arg Met Ile Pro
1               5                   10

( 2 ) INFORMATION FOR SEQ ID NO:9:

( i ) SEQUENCE CHARACTERISTICS:
        ( A ) LENGTH: 7 amino acids
        ( B ) TYPE: amino acids
        ( C ) STRANDEDNESS: unknown
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:9:

Ala Leu Asn Xaa Arg Phe Gly
1               5

( 2 ) INFORMATION FOR SEQ ID NO:10:

( i ) SEQUENCE CHARACTERISTICS:
        ( A ) LENGTH: 22 amino acids
        ( B ) TYPE: amino acids
        ( C ) STRANDEDNESS: unknown
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:10:

Phe Gln Leu Thr Glu Gln Phe Leu Thr Glu Asp Tyr Ala Asn Asn Gly
1               5                   10                  15

Ile Glu Leu Asn Asn Arg
            20

( 2 ) INFORMATION FOR SEQ ID NO:11:

( i ) SEQUENCE CHARACTERISTICS:
        ( A ) LENGTH: 11 amino acids
        ( B ) TYPE: amino acids
        ( C ) STRANDEDNESS: unknown
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:11:

```
Tyr  Gln  Arg  Val  Ser  Asn  Ala  Ile  Gly  Asn  Arg
 1                  5                        10
```

( 2 ) INFORMATION FOR SEQ ID NO:12:

( i ) SEQUENCE CHARACTERISTICS:
        ( A ) LENGTH: 132 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( i x ) FEATURE:
        ( A ) NAME/KEY: Coding Sequence
        ( B ) LOCATION: 1...132

( x i ) SEQUENCE DESCRIPTION: SEQ ID NO:12:

```
TTT  CAA  CTC  ACA  GAA  CAA  TTT  TTG  ACT  GAG  GAC  TAC  GCC  AAC  AAC  GGC      48
Phe  Gln  Leu  Thr  Glu  Gln  Phe  Leu  Thr  Glu  Asp  Tyr  Ala  Asn  Asn  Gly
 1                   5                        10                       15

ATC  GAA  TTA  AAC  AAC  CGT  TTC  GGT  GAC  GAT  GCT  TCT  GAG  AAG  ATA  CCC      96
Ile  Glu  Leu  Asn  Asn  Arg  Phe  Gly  Asp  Asp  Ala  Ser  Glu  Lys  Ile  Pro
                     20                       25                       30

CTC  AAG  AAC  CTC  AGC  AAA  CTC  CCA  GAA  TTT  AAA  ATT                          132
Leu  Lys  Asn  Leu  Ser  Lys  Leu  Pro  Glu  Phe  Lys  Ile
                     35                       40
```

( 2 ) INFORMATION FOR SEQ ID NO:13:

( i ) SEQUENCE CHARACTERISTICS:
        ( A ) LENGTH: 63 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( i x ) FEATURE:
    ( A ) NAME/KEY: Coding Sequence
    ( B ) LOCATION: 1...63

( x i ) SEQUENCE DESCRIPTION: SEQ ID NO:13:

| TAC | CAG | CGT | GTG | TCA | AAT | GCT | ATA | GGC | AAC | AGG | TTC | GGT | AGC | GAC | GCG | 48 |
|---|---|---|---|---|---|---|---|---|---|---|---|---|---|---|---|---|
| Tyr | Gln | Arg | Val | Ser | Asn | Ala | Ile | Gly | Asn | Arg | Phe | Gly | Ser | Asp | Ala | |
| 1 | | | | 5 | | | | | 10 | | | | | 15 | | |

| GGC | CGC | ATG | ATA | CCC | 63 |
|---|---|---|---|---|---|
| Gly | Arg | Met | Ile | Pro | |
| | | | 20 | | |